United States Patent
Lovett et al.

(10) Patent No.: US 11,375,985 B2
(45) Date of Patent: Jul. 5, 2022

(54) SYSTEMS AND METHODS FOR AN ULTRASOUND-GUIDED PERCUTANEOUS NEPHROSTOMY MODEL

(71) Applicant: Arizona Board of Regents on Behalf of The University of Arizona, Tucson, AZ (US)

(72) Inventors: Marissa Lovett, Tucson, AZ (US); David E. Biffar, Tucson, AZ (US); Allan J. Hamilton, Tucson, AZ (US); David T. Tzou, Tucson, AZ (US); Michael Phung, Tucson, AZ (US); Benjamin R. Lee, Tucson, AZ (US)

(73) Assignee: Arizona Board of Regents on Behalf of the University of Arizona, Tucson, AZ (US)

( * ) Notice: Subject to any disclaimer, the term of this patent is extended or adjusted under 35 U.S.C. 154(b) by 0 days.

(21) Appl. No.: 17/606,508

(22) PCT Filed: May 1, 2020

(86) PCT No.: PCT/US2020/031085
§ 371 (c)(1),
(2) Date: Oct. 26, 2021

(87) PCT Pub. No.: WO2020/227118
PCT Pub. Date: Nov. 12, 2020

(65) Prior Publication Data
US 2022/0142617 A1    May 12, 2022

Related U.S. Application Data

(60) Provisional application No. 62/843,060, filed on May 3, 2019.

(51) Int. Cl.
*G09B 23/28* (2006.01)
*A61B 8/00* (2006.01)

(52) U.S. Cl.
CPC ............ *A61B 8/587* (2013.01); *G09B 23/285* (2013.01); *G09B 23/286* (2013.01)

(58) Field of Classification Search
CPC ....... G09B 23/28; G09B 23/285; G09B 23/30
See application file for complete search history.

(56) References Cited

U.S. PATENT DOCUMENTS

| 5,055,051 A | 10/1991 | Duncan |
| 6,939,138 B2 | 9/2005 | Chosack et al. |

(Continued)

FOREIGN PATENT DOCUMENTS

| CN | 203217860 U | 4/2013 |
| ES | 2683068 A1 | 3/2017 |

(Continued)

OTHER PUBLICATIONS

International Search Report and Written Opinion in corresponding Application No. PCT/US2020/031085 dated Aug. 3, 2020, 8 pages.

(Continued)

*Primary Examiner* — Kurt Fernstrom
(74) *Attorney, Agent, or Firm* — Polsinelli PC

(57) ABSTRACT

An anatomical model includes a first container, a second container disposed within the first container, and a third container disposed within the second container. The second container and the third container simulate components of kidney anatomy, and the model includes ballistics gel to improve echogenicity during an ultrasound-guided training procedure using the model.

20 Claims, 7 Drawing Sheets

(56) References Cited

U.S. PATENT DOCUMENTS

| | | | |
|---|---|---|---|
| 7,059,168 B2 * | 6/2006 | Hibi | G09B 23/306 |
| | | | 434/272 |
| 7,943,231 B2 * | 5/2011 | Kawabata | A61B 8/587 |
| | | | 434/273 |
| 8,480,407 B2 * | 7/2013 | Campbell | G09B 23/28 |
| | | | 434/272 |
| 8,911,238 B2 * | 12/2014 | Forsythe | G09B 23/28 |
| | | | 434/267 |
| 9,564,068 B2 | 2/2017 | Redaelli et al. | |
| 10,083,632 B2 | 9/2018 | Ristolainen et al. | |
| 2011/0319758 A1 | 12/2011 | Wang | |
| 2012/0015339 A1 * | 1/2012 | Hendrickson | G09B 23/303 |
| | | | 434/273 |
| 2013/0122477 A1 | 5/2013 | Everett | |
| 2015/0037776 A1 * | 2/2015 | Redaelli | G09B 23/28 |
| | | | 434/272 |
| 2015/0056591 A1 * | 2/2015 | Tepper | G09B 23/286 |
| | | | 434/262 |
| 2015/0086955 A1 * | 3/2015 | Poniatowski | G06T 7/0014 |
| | | | 434/262 |
| 2017/0278429 A1 | 9/2017 | Slanda et al. | |
| 2019/0130791 A1 * | 5/2019 | Qiu | G09B 23/285 |

FOREIGN PATENT DOCUMENTS

| | | |
|---|---|---|
| GB | 2328775 A | 3/1999 |
| RU | 2691524 C1 | 6/2019 |

OTHER PUBLICATIONS

Shamah, et al., A 5-Dollar Nephrostomy Training Phantom Using Common Household and Hospital Supplies, Nov. 2017. [Online] Retrieved from < URL: https://wwwultrasoundtraining.com.au/wp-content/uploads/2020/03/2017-Shamah-nephrostomy-sim.pdf > col. 2 of p. 1613 onward.

O'Reilly, et al., Fabrication and Assessment of 3D Printed Anatomical Models of the Lower Limb for Anatomical Teaching and Femoral Vessel Access Training in Medicine. Jun. 24, 2015. [Online] Retrieved from < URL: https://epub.ub.uni-muenchen.de/36519/1/10.1002_ase.1538.pdf > entire document, especially pp. 74 and 77.

Shamah et al., A 5-Dollar Nephrostomy Training Phantom Using Common Household and Hospital Supplies JVIR, vol. 28, No. 11, Nov. 2017, pp. 1613-1615.

PCNL Kidney Trainer, Encoris, [online] https://encoris.com/pcnl-kidney-trainer/, 7 pages, 2021.

* cited by examiner

SYSTEMS AND METHODS FOR AN ULTRASOUND-GUIDED PERCUTANEOUS NEPHROSTOMY MODEL

CROSS REFERENCE TO RELATED APPLICATIONS

This is a PCT application that claims benefit to U.S. provisional application Ser. No. 62/843,060 filed on May 3, 2019, which is incorporated by reference in its entirety.

FIELD

The present disclosure generally relates to embodiments of an anatomical model for ultrasound-guided procedures, including an ultrasound-guided percutaneous nephrostomy model.

BACKGROUND

In the field of urology, percutaneous nephrolithotomy (PCNL) involves obtaining percutaneous access into the collecting system portion of the kidney to treat large kidney stone burden (>2 cm). Traditionally, this operation has relied on fluoroscopy, thereby exposing the patient and the operative staff to ionizing radiation. Recently, centers of excellence have demonstrated that this operation can be performed under only ultrasound with zero radiation exposure. However, the shift to ultrasound requires surgeons to adapt quickly to different ways of using technology. As such, there is a high demand for ultrasound-guided PCNL training.

It is believed that existing training models lack sufficient technical features for urology residents and attending physicians to adequately absorb this ultrasound-guided PCNL training. For example, current training models are structurally suboptimal, generally expensive, and narrowly focused (on, e.g., mimicking fluoroscopic renal access). Further, these models lack key anatomical features, as described herein.

It is with these observations in mind, among others, that various aspects of the present disclosure were conceived and developed.

BRIEF DESCRIPTION OF THE DRAWINGS

The application file contains at least one photograph executed in color. Copies of this patent application publication with color photographs will be provided by the Office upon request and payment of the necessary fee.

Corresponding reference characters indicate corresponding elements among the view of the drawings. The headings used in the figures do not limit the scope of the claims.

DETAILED DESCRIPTION

The present disclosure generally relates to an anatomical model and methods thereof to assist with training for ultrasound-guided medical procedures. In some embodiments, the anatomical model includes a nephrostomy model formed for surgical training during ultrasound-guided procedures, such as ultrasound-ablation of kidney stones. Accordingly, the present nephrostomy model may include simulated or artificial kidney components such as a general kidney structure, kidney stones, ribs, paraspinous muscle, fluid drip, and the like. The nephrostomy model may be formed as a general model for training, and may also take the form of a patient-specific nephrostomy model with anatomical components formed consistent with imaging data associated with a specific patient.

The present nephrostomy model improves upon prior models because the present nephrostomy model incorporates numerous anatomical features advantageous for training of PCNL during ultrasound procedures, and overcomes technical issues presented by existing models, which allows surgeons or other medical professionals to be better prepared to perform the crucial operative steps to safely perform PCNL with ultrasound during live procedures. Moreover, the model can be formed and operated at a fraction of the cost of existing models.

In some embodiments, the model includes a calyx system, parenchyma, soft tissues, anatomical landmarks, and a container such as a box, among other features. At least some of the features of the nephrostomy model may be summarized as follows:

Kidney structure: A realistic kidney representation allows for an operator to have tactile and visual feedback as a needle progresses through the capsule, cortex, and into the calyces. Kidney targets represent the small amount of urine present between the kidney stone and edge of the calyx. These are the crucial visual cues to achieve safe access into the desired calyx.

Kidney stones: The ability to mimic visual representation of kidney stones on ultrasound is crucial to replicating the operative experience for PCNL.

Ribs: Ribs provide both a superficial tactile anatomic landmark, as well as an acoustic shadow within the ultrasound image. This mimics the challenges faced by the operator of optimally imaging the kidney to achieve needle access. The ribs may be anatomically positioned over the kidney.

Paraspinous muscle: This muscle layer provides another anatomic landmark to mimic correct ultrasound probe positioning to image the kidney.

Fluid drip: Fluid drip provides immediate visual feedback of proper positioning of the needle in the desired target calyx.

A study follows the description of the model. The study illustrates the model fidelity and describes the initial experience of the model in training urology students.

Figure 1:
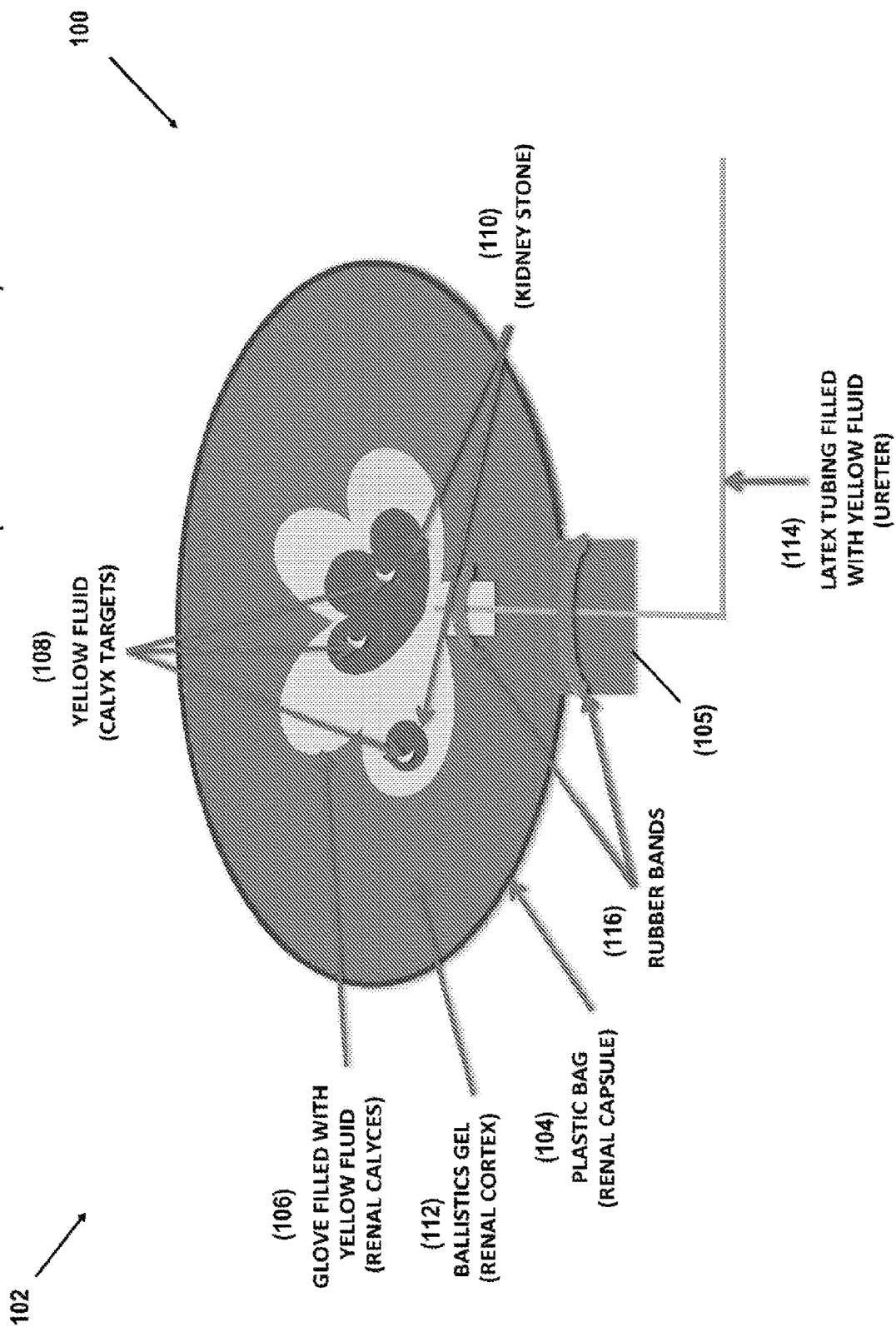
FIG. 1 is a simplified image of a general artificial kidney structure for use with ultrasound-guided procedure training.

Referring to FIG. 1, an overall general nephrostomy model 100 (shown in FIG. 2) may include and be generally formed around an artificial kidney structure ("kidney" or "kidney anatomy") 102. In some embodiments, the kidney 102 includes a renal capsule 104 in the form of a bag or other such flexible container (e.g., formed with plastic or other such material) having a predetermined shape configuration resembling a natural kidney structure, which may define an opening 105 as shown. As further indicated in FIG. 1, the kidney 102 may generally include one or more of a renal calyx 106 which may be in the form of a surgical glove (or other container) disposed within the renal capsule 104 and at least partially filled with a yellow fluid 108 (e.g., water with yellow food coloring) to simulate renal calyces and calyx targets, as further described herein. In addition, one or more artificial kidney stones 110 (formed using calcium carbonate or other such material) may be disposed within the renal calyx 106 and submerged within the yellow fluid 108.

In some embodiments, the renal capsule 104 may be at least partially filled with ballistics gel 112 to resemble a renal cortex. Further, a tube 114 formed with latex or other such material, may be filled with a yellow fluid, and may be partially introduced to within the interior of the renal capsule 104 through the opening 105 as shown to simulate a natural ureter. As further shown, one or more rubber bands 116 or other such fastening members may be applied to the renal calyx 106 or to the renal capsule 104 to maintain the contents of the kidney 102 described within each respective component.

Figure 2:
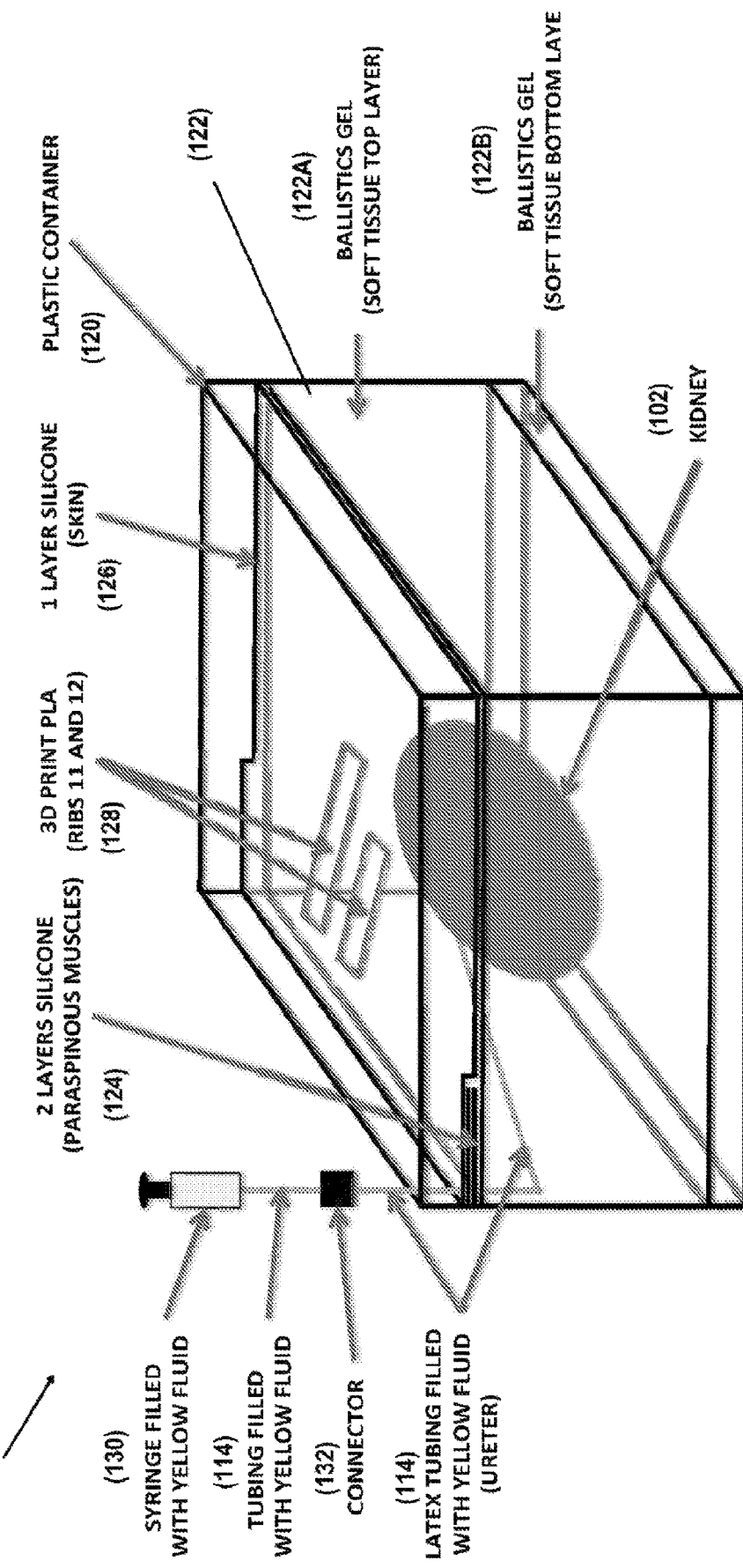
FIG. 2 is a simplified image of a general nephrostomy model including the artificial kidney structure of FIG. 1 for use with ultrasound-guided procedure training.

Referring to FIG. 2, the kidney 102 may be suspended at a general centermost (or other predetermined) position within a container 120 using a predetermined amount of ballistics gel 122, as indicated and further described herein, such that the kidney is partially or totally encapsulated within the ballistics gel 122. In some embodiments, the container 120 may be at least partially transparent such that contents within the container 120 including the kidney 102 can be observed from different angles. Suspending the kidney 102 within the container 120 as described accommodates real world training with the general nephrostomy model 100 because, e.g., a surgeon may simulate a situation where a needle is passed entirely through the kidney 102 accidently and visually observe this situation. This observation may not be possible if the kidney rested along the bottom of the container 120 where passing the needle through the top side of the kidney 102 may result in the needle making contact with the bottom of the container 120, presenting an obstruction uncommon within a natural clinical setting.

As further shown in FIG. 2, the ballistics gel 122 may include two different layers of ballistics gel, represented as ballistics gel layer 122A and ballistics gel layer 122B, which may simulate a soft tissue top layer and a soft tissue bottom layer, respectively. In addition, a layer 124 may be formed within the container 120 to simulate paraspinous muscles, and a layer 126 may be formed along the container 120 over the layer 124 to simulate skin tissue, and each of the layer 124 and the layer 126 may be formed with silicone or other similar material. In some embodiments, three-dimensional (3D) ribs 128 may be printed to resemble ribs 11 and 12, which may also be disposed within the container 120 as indicated. FIG. 2 further illustrates that a syringe 130 may be coupled to the tube 114 via a connector 132 or otherwise to introduce the yellow fluid 108 to within portions of the model 100 as described herein. As indicated herein, the container 120 may define a first container (e.g., box), the renal capsule 104 may define or be generally formed using a second container (e.g., bag) disposed within the first container (120), and the renal calyx 106 may define or be generally formed using a third container disposed within the second container (e.g., glove).

Figure 3:
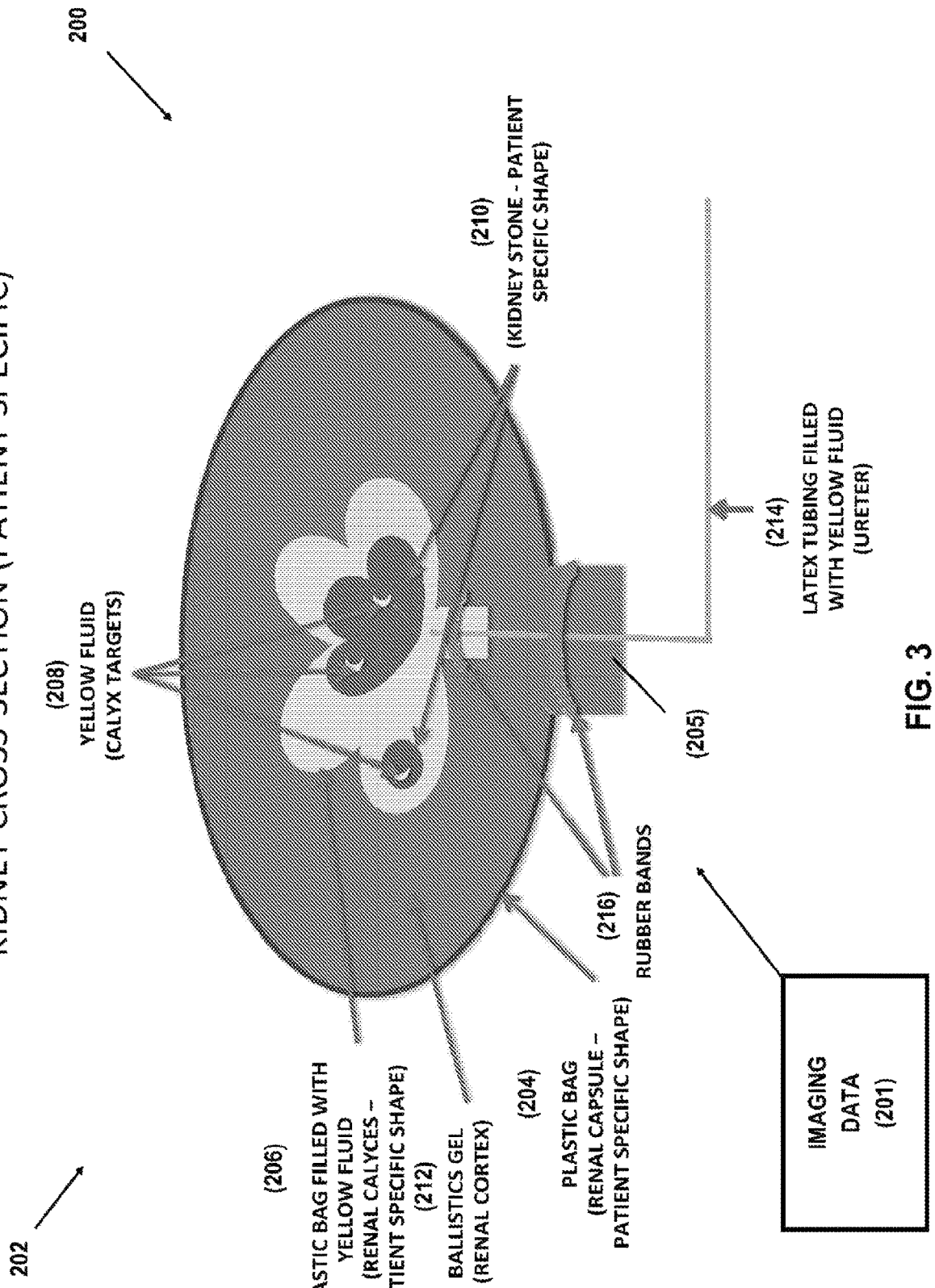
FIG. 3 is a simplified image of a patient-specific artificial kidney structure for use with ultrasound-guided procedure training.

Referring to FIG. 3, a patient-specific nephrostomy model 200 (shown in FIG. 4) may include and be generally formed around an artificial kidney structure ("kidney") 202. In this embodiment, the kidney 202 and the model 200 as a whole may be formed with dimensions and specifications consistent with imaging data 201 associated with a specific patient, so that the model 200 ultimately at least closely resembles the natural kidney of the patient, and also resembles any abnormalities of the patient such as kidney stones. The kidney 202 may generally comprise a renal capsule 204 (formed using bag comprised of plastic or other such material) having a predetermined shape configuration resembling a patient-specific kidney structure, which may define an opening 205 as shown. As further indicated in FIG. 3, the kidney 202 may generally include a renal calyx or calyces 206 in the form of a glove or other such container disposed within the renal capsule 204 and at least partially filled with a yellow fluid 208 to simulate natural renal calyces and calyx targets, as further described herein. In addition, one or more artificial kidney stones 210 may be disposed within the renal calyx 206 and submerged within the yellow fluid 208. Utilizing the imaging data 201 of the specific patient, the kidney stones 210 may be formed to resemble natural kidney stones present within the patient including the same or similar specifications and size, as further described herein.

In some embodiments, the renal capsule 204 may be at least partially filled with ballistics gel 212 to resemble a renal cortex. Further, a tube 214 formed of latex or other such material, may be filled with a yellow fluid and may be partially introduced to within the interior of the renal capsule 204 through the opening 205 as shown to simulate a natural ureter. As further shown, one or more rubber bands 216 or other such fastening members may be applied to the renal calyx 206 and/or to the renal capsule 204 to maintain the contents within each respective component.

Figure 4:
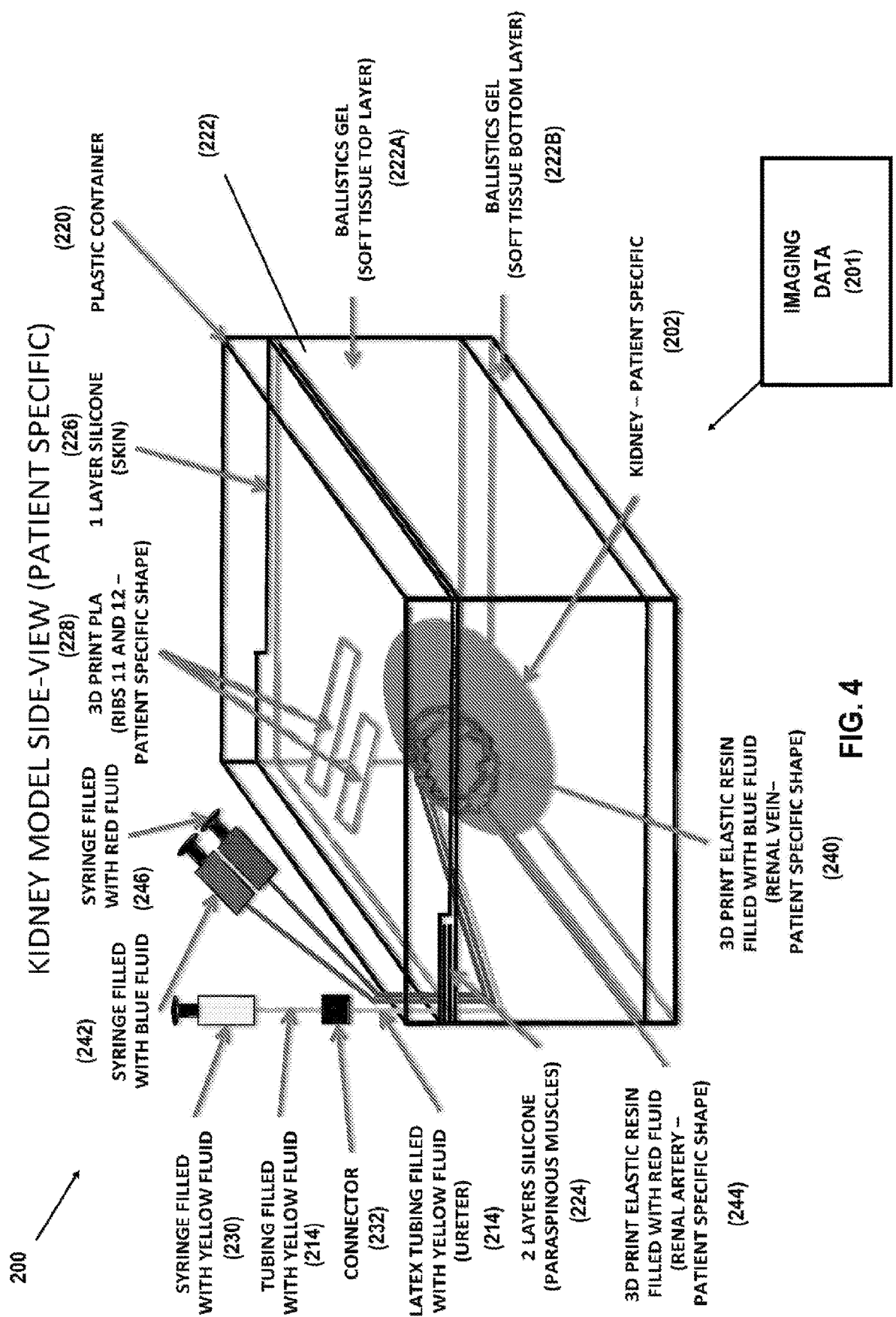
FIG. 4 is a simplified image of a patient-specific nephrostomy model including the artificial kidney structure of FIG. 1 for use with ultrasound-guided procedure training.

Referring to FIG. 4, the kidney 202 may be suspended at a general centermost position within a container 220 using a predetermined amount of ballistics gel 222, as indicated and further described herein. In some embodiments, the container 220 may be at least partially transparent such that contents within the container 220 including the kidney 202 can be observed. Suspending the kidney 202 within the container 220 as described accommodates real world training with the patient-specific nephrostomy model 200 because, e.g., a surgeon may simulate a situation where a needle is passed entirely through the kidney 202 accidently and visually observe this situation. This observation may not be possible if the kidney 202 rested along the bottom of the container 220 where passing the needle through the top side of the kidney 202 may result in the needle making contact with the bottom of the container 220, presenting an obstruction uncommon within a natural clinical setting.

As further shown in FIG. 4, the ballistics gel 222 may include two different layers of ballistics gel, represented as ballistics gel layer 222A and ballistics gel layer 222B, which may simulate a soft tissue top layer and a soft tissue bottom layer, respectively. In addition, a layer 224 may be formed within the container 220 to simulate paraspinous muscles, and a layer 226 may be formed along the container 220 to simulate or resemble skin tissue; each of the layer 224 and the layer 226 comprising silicone or other such material. In some embodiments, three-dimensional (3D) ribs 228 may be printed to resemble ribs 11 and 12 of a patient-specific shape, which may also be disposed within the container 220 as indicated. FIG. 4 further illustrates that a syringe 230 may be coupled to the tube 214 via a connector 232 or otherwise to introduce the yellow fluid 208 to within portions of the model 200 as described herein.

In addition, the model 200 may be formed with additional various patient-specific anatomical components. For example, renal veins 240 may be formed within the container 220 and may take the form of a 3D printed elastic resin member, filled with a blue fluid (introduced via a syringe 242 or otherwise) to resemble natural renal of the patient. Further, renal arteries 244 may be formed within the container 220 and may take the form of a 3D printed elastic resin member, filled with a red fluid (introduced via a syringe 246 or otherwise) and may resemble natural rental arteries of the patient.

Figure 5:
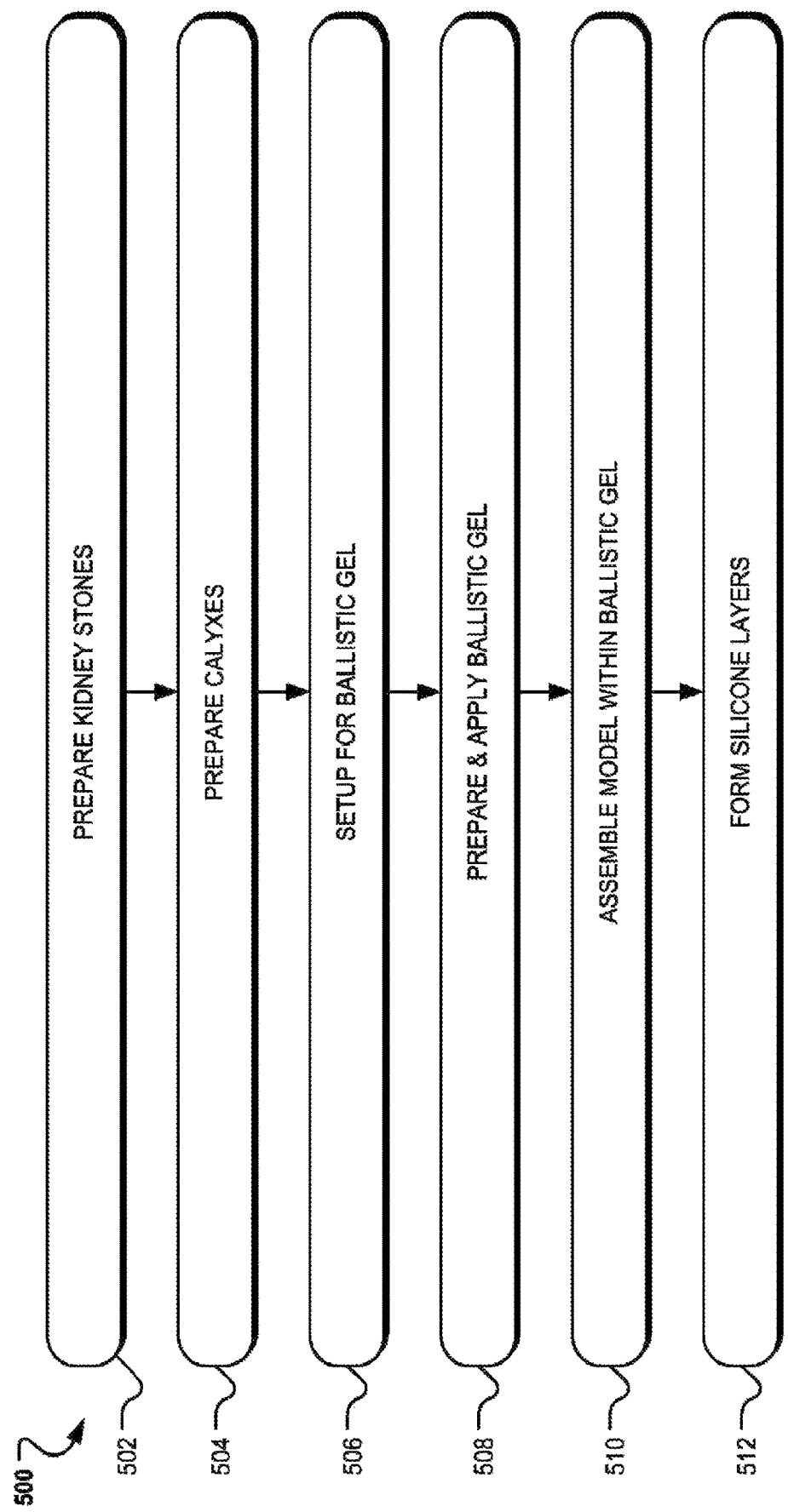
FIG. 5 is a simplified block diagram illustrating a possible process flow for forming the general nephrostomy model depicted in FIGS. 1-2.

Referring to FIG. 5, a sample process flow for forming the general ultrasound percutaneous nephrostomy training model (nephrostomy model) 100 of FIG. 2 is illustrated. Referring to block 502, one or more artificial kidney stones 110 may be formed. In some embodiments, the artificial kidney stones 110 may resemble ~1.5 cm stones and/or a ~3 cm pelvis staghorn. This step may involve accessing a predetermined amount of calcium carbonate in powder form (e.g., by crushing Tums® tablets). In some embodiments, the calcium carbonate may be disposed within the renal calyx 106, which may be a 6.0 nitriderm glove, and any opening of the calyx 106 may be tied off or otherwise covered using the rubber bands 116 or otherwise. In some embodiments, excess fingertips of the glove used to resemble the calyx 106 may be cut off or removed, the artificial staghorn stone may be superglued to itself to create 3D calyces, the kidney stones 110 may be superglued in place within the renal calyx 106, and the calyx 106 may be flipped, such that the kidney stones 110 are on the inside portion of the calyx 106.

Referring to block 504, artificial calyxes may be prepared. Specifically, in some embodiments, the tubing 114, comprising a general latex tube (which may be '50 cm long) may be introduced into the base of the calyx 106. The tube 114 may then be secured in place relative to the calyx 106 using one or more of the rubber bands 116 or other fastener, and a coupling or connector 132 may be attached to the free end of the tube to form a glove-tube system. In this step, the syringe 130 may be employed to remove most of the air from the glove-tube system, and the syringe 130 may also be used to fill the glove-tube system with the yellow-dyed water or yellow fluid 108. Remaining air may also be entirely removed from the glove-tube system.

Referring to block 506, the model 100 may be prepared for introduction of ballistic gel, which may be poured to within the container 120 and also possibly introduced to within various anatomical components of the model 100 as described herein. For example, the glove-tube system (calyx 106) may be set up for the introduction of ballistic gel for forming aspects of the nephrostomy model 100. In this step, the calyx 106 (glove) may be suspended within a quarter zip lock bag (renal capsule 104), and a funnel may be added to the top of the glove representing the calyx 106. In addition, the top of the glove representing the calyx 106 may be sealed off with a rubber band 116 or otherwise, such that only the tube 114 and funnel exit the calyx 106).

Referring to block 508, a predetermined amount of ballistic gel 122 may be prepared for forming aspects of the nephrostomy model 100. In this step, a multicooker may be employed to preheat water to approximately 75 degrees Celsius, and a portion of the water may be disposed within a beaker. The total volume of the water preheated and disposed within the beaker may include enough heated water to fill the zip lock bag (~400 ml) or other container forming the renal capsule 104, and a predetermined volume of the water may be reserved for the container 120 (~600 ml). A predetermined amount of the ballistic gel 122 may then be introduced to the preheated water in the beaker. In some embodiments, 100 g of the ballistic gel 122 may be introduced for every 800 ml of the preheated water. The contents of the beaker, i.e., the ballistic gel-water solution, may be transferred to a cooking pot to maintain heat, where the solution can be stirred for approximately ten minutes. In some embodiments, cornstarch may be applied to the ballistic gel solution and stirred in at a predetermined ratio, which may be 9 g/l of the solution. In some embodiments, the cornstarch may be smoothed in advance by introducing predetermined small amounts of ballistic gel to the cornstarch before the cornstarch is introduced to the solution.

Referring to block 510, in some embodiments, the ballistics gel 122 may be poured into the container 120 to form the ballistics gel layer 122B, or bottom layer, and the kidney 102 may be disposed over, or partially submerged within the ballistics gel layer 122B, such that the kidney 102 is at least partially suspended over the bottom of the container 120, i.e., at least some space remains between the bottom of the container 120 and the kidney 102. In some embodiments, the ballistics gel layer 122B may be permitted to cool before introduction of the kidney 102 or other anatomical components to decrease the possibility of heat damage. In addition, the other anatomical components of the model 100 may be introduced, such as the 3D printed ribs 128, the ballistics gel layer 122A, etc.

Referencing block 512, one or more silicone layers simulating skin tissue and/or paraspinous muscles may be formed along the model 100. Specifically, for example, a layer of silicone 126 representing skin tissue may be applied to the model 100, and a silicone layer 124 may be applied to represent paraspinous muscles. Both of the silicone layer 124 and the silicone layer 126 may be formed using Dragon Skin® products such as Fast (Smooth On) tinted with a predetermined skin color. In particular, the Dragon Skin Fast (Smooth On) may first be applied along a flat surface as a general layer, and the Dragon Skin Fast layer may be covered with baby powder or other such similar components to reduce adhesion to the flat surface. Once the model 100 and the Dragon Skin Fast (Smooth On) have cured, the Dragon Skin Fast layer may then be cut to extract the silicone layer 126. In some embodiments, the silicone layer 124 may be formed using one or more strips of the Dragon Skin Fast layer.

Figure 6:
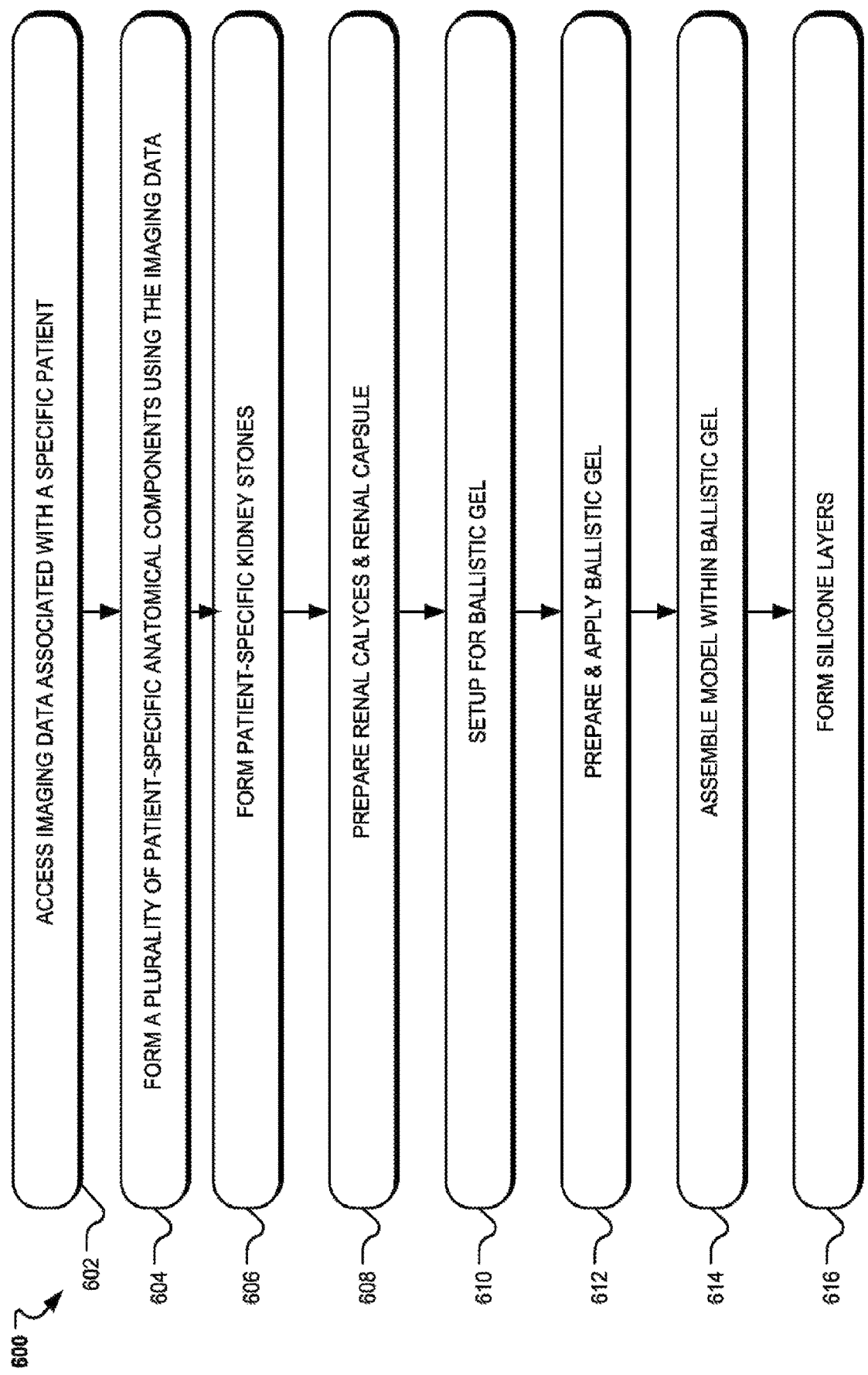
FIG. 6 is a simplified block diagram illustrating a possible process flow for forming the patient-specific nephrostomy model depicted in FIGS. 3-4.

Referring to FIG. 6, a sample process flow for forming the patient-specific ultrasound percutaneous nephrostomy training model (nephrostomy model) 200 of FIG. 3 is illustrated. Referring to block 602, imaging data 201 associated with a specific patient may be generated and/or accessed. In some embodiments, the imaging data 201 may include DICOM (Digital Imaging and Communications in Medicine) images from a patient CT scan, or other such data.

Referring to block 604, a plurality of anatomical components may then be formed or assembled using the imaging data 201. For example, the patient's 11th and 12th ribs (228), kidney stones (210), one or more renal calyces (206), a renal capsule (204), a renal vein (240), and a renal artery (244) may be formed using, e.g., 3D slicer software. In addition, any of the aforementioned components may be 3D printed using PLA from, e.g., a Lulzbot extruder printer, or via injection molding, or otherwise.

In some embodiments, the patient's renal artery 244 and renal vein 240 may be 3D printed with resin on a Formlabs printer. CAD information for the renal artery 244 and renal vein 240 may be edited to define a loop configuration for each component that extends outside of the container 220, which may allow fluid to be pushed through these simulated vessels to represent blood and vascular flow.

In some embodiments, a coupling may be attached to the ends of the blood vessels (the patient's renal artery 244 and renal vein 240) and syringes may be attached to the blood vessels (syringe 242 and syringe 246), so that red-dyed water may be injected to within the renal artery 244 using the syringe 246, and blue-dyed water may be injected into the renal vein 240 using the syringe 242. Further, excess air may be removed from the patient's renal artery 244 and renal vein 240.

Referring to block 606, one or more kidney stones 210, which may be patient-specific, may be formed. In some embodiments, a clay mold may be manufactured for forming the kidney stones 210 using the imaging data 201 or otherwise. In addition, calcium carbonate may be accessed in powder form by, e.g., crushing Tums tablets or otherwise. Water may then be stirred into the calcium carbonate powder to form a mixed solution or paste, or "calcium carbonate mixture." The calcium carbonate mixture may then be poured into the clay mold, and the mold may be baked to evaporate excess water. In some embodiments, the resulting kidney stones 210 may be coated with an aerosolized liquid rubber coating, such as FlexSeal.

Referring to block 608, the renal calyces 206 may be 3D printed using the imaging data 201. In some embodiments, a wire may be wrapped around the printed renal calyces 206, and the wire may be heated with a heat gun. In addition, the heated wire may be placed along two sheets of thin plastic to seal the sheets together (e.g., Ziploc; or polyethylene). The pelvis side of the renal calyces 206 may remain open to allow insertion of the kidney stones 210. In other words, one or more of the kidney stones 210 may be inserted within the renal calyces 206 and fixed in places relative to the renal calyces 206 using superglue or other form of adhesion or by way of a securing member.

In some embodiments, the tube 214 may then be inserted into the base of the renal calyces 206. The tube 214 may be secured in place using one of the rubber bands 216 or other mechanism, and a coupling may be attached to the free end of the tube 214. Further, a syringe may be employed to remove air from the tube 214, and yellow-dyed water may be introduced into the tube 214 and into the renal calyces 206.

As further indicated in block 608, the renal capsule 204 may be prepared and added to the model 200. In some embodiments, a wire may be wrapped about a periphery of the 3D printed renal capsule 204, and the wire may be heated using a heat gun or otherwise. In addition, the heated wire may be placed along two sheets of thin plastic to seal the sheets together (e.g., Ziploc; and/or polyethylene), and the ureter side of the renal capsule 204 may be left open to allow for insertion of the renal calyces 206.

Referring to block 610, a predetermined amount of ballistic gel 222 may be prepared for forming aspects of the patient-specific nephrostomy model 200. In this step, a multicooker may be employed to preheat water to approximately 75 degrees Celsius, and a portion of the water may be disposed within a beaker. The total volume of the water preheated and disposed within the beaker may include enough heated water to fill the zip lock bag (~400 ml) and a predetermined volume of the water may be reserved for the container 220 (~600 ml). A predetermined amount of the ballistic gel 222 may then be introduced to the preheated water in the beaker. In some embodiments, 100 g of the ballistic gel 222 may be introduced for every 800 ml of the preheated water. The contents of the beaker, i.e., the ballistic gel-water solution, may be transferred to a cooking pot to maintain heat, where the solution can be stirred for approximately ten minutes. In some embodiments, cornstarch may be applied to the ballistic gel solution and stirred in at a predetermined ratio, which may be 9 g/l of the solution. In some embodiments, the cornstarch may be smoothed in advance by introducing predetermined small amounts of ballistic gel to the cornstarch before the cornstarch is introduced to the solution.

Referring to block 612, in some embodiments, the ballistics gel 222 may be poured into the container 220 to form the ballistics gel layer 222B, or bottom layer, and the kidney 202 may be disposed over, or partially submerged within the ballistics gel layer 222B, such that the kidney 202 is at least partially suspended over the bottom of the container 220, i.e., at least some space remains between the bottom of the container 220 and the kidney 202. In some embodiments, the ballistics gel layer 222B may be permitted to cool before introduction of the kidney 202 or other anatomical components to decrease the possibility of heat damage. In addition, the other anatomical components of the model 200 may be introduced, such as the 3D printed ribs 228, the ballistics gel layer 222A, etc.

In addition, in some embodiments, a predetermined amount of the ballistics gel 222 may be poured into the renal capsule 204 using a funnel or otherwise. The renal capsule 204 may then be sealed until the ballistics gel 222 fully solidifies.

Referring to block 614, one or more of the anatomical components of the model 200 may be assembled. For example, the renal artery 244 and the renal vein 240 may be secured around the renal capsule 204 using tape or other means of adhesion. The kidney 202 (renal capsule 204, renal artery 244 and the renal vein 240) may be secured along or proximate to the base of the container 220 using tape or other means of adhesion. The ribs 228 may be assembled along the kidney 202 such that the upper tip portion of the kidney 202 lies between the ribs 11 and 12 of the ribs 228. The ribs 228 may be taped across the top left corner of the model 200 such that the ribs 228 are approximately 1.75 cm apart, and lay flat along the model 200.

Referring to block 616, one or more silicone layers simulating skin tissue and/or paraspinous muscles may be formed along the model 200. Specifically, for example, a layer of silicone 226 representing skin tissue may be applied to the model 200, and a silicone layer 224 may be applied to represent paraspinous muscles. Both of the silicone layer 224 and the silicone layer 226 may be formed using Dragon Skin Fast (Smooth On) tinted with a predetermined skin color. In particular, the Dragon Skin Fast (Smooth On) may first be applied along a flat surface, and the layer may be covered with baby powder or other such similar components to reduce adhesion to the flat surfaced. Once the model 200 and the Dragon Skin Fast (Smooth On) have cured, the layer may then be cut to extract the silicone layer 226. In some embodiments, the silicone layer 224 may be formed using one or more strips of the Dragon Skin Fast layer.

Either of the model 100 or the model 200 is well suited for training during ultra-sound guided procedures associated with the kidney and surrounding anatomy. Implementation of the ballistic gel is believed to be of particular importance because the material is suitable for ultra-sound signal interpretation and is echogenic; i.e., the ballistic gel provides improved feedback to the clinician when interacting with either of the model 100 or the model 200 under ultra-sound procedure training.

Figure 7:
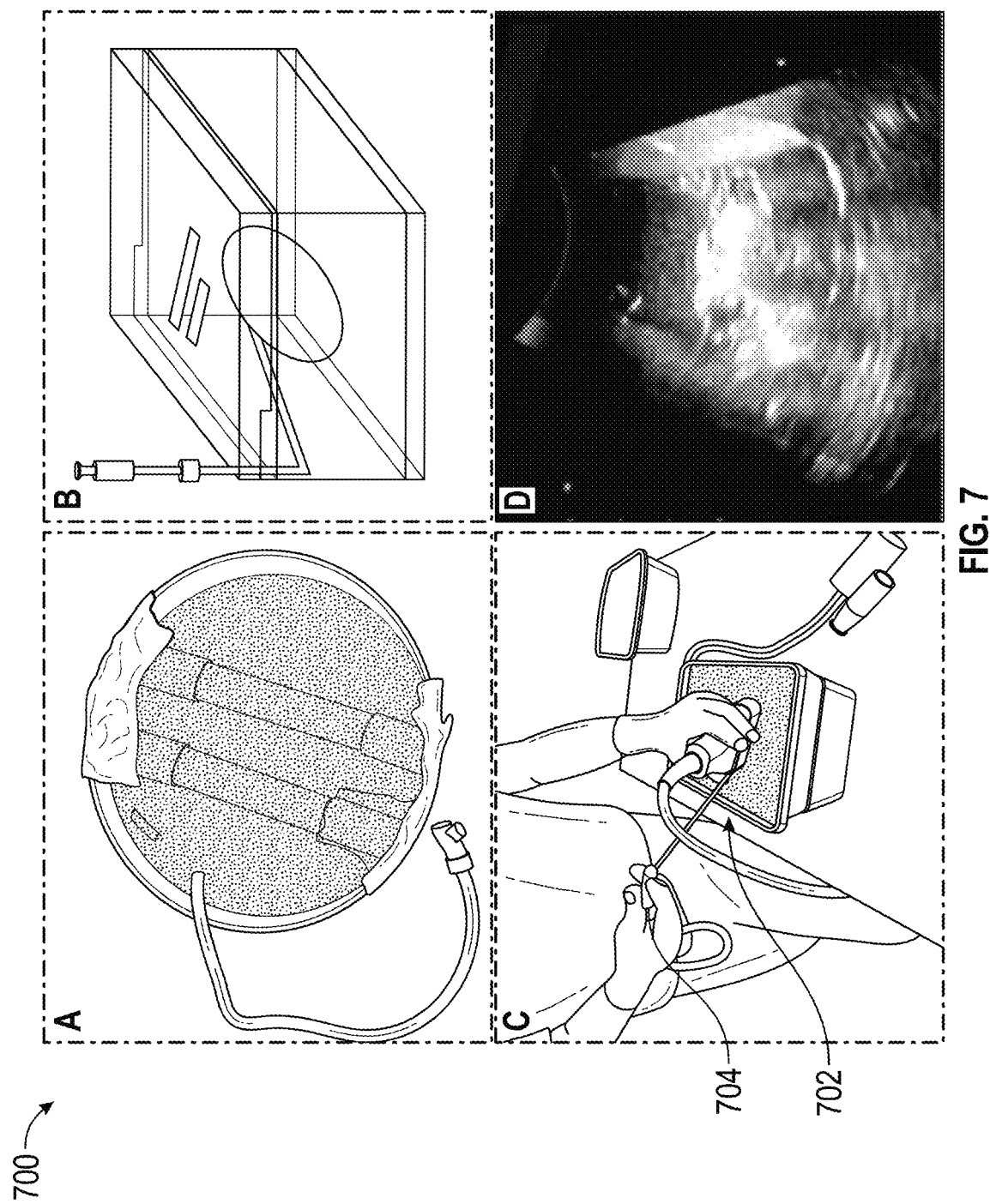
FIG. 7A is a photograph of a preliminary design phase of an embodiment of the model described herein.
FIG. 7B is a general illustration or design diagram of an embodiment of the model described herein.
FIG. 7C is a photograph of an embodiment of the model described herein in use during a needle insertion procedure.
FIG. 7D is an ultrasound image used with the procedure shown in FIG. 7C.

Referring to FIG. 7, an ultrasound-guided percutaneous nephrolithotomy (US-PCNL) model ("model") 700 shall now be described, which generally incorporates the features of the models 100 and 200 and is a specific non-limiting embodiment which was formed and implemented for a study described herein. It is contemplated that features of the model 700 may be incorporated within any of the models 100 and 200, and likewise, the model 700 may incorporate one or more features of the models 100 and 200. In other words, the models 100, 200, and 700 are not mutually exclusive with respect to implementation of features, and these models are related embodiments which share the same or similar novel features.

Like the models 100 and 200, the model 700 includes a container or box (e.g., a first container such as container 120). The container, for example, may be a plastic, resealable container such as 9×7.25×5.25 inches). These dimensions were chosen to allow proper depth of the kidney and sufficient room for needle placement, while optimizing the use of ballistics gel. The resealable nature of the container accommodates extended refrigerated shelf life of the model to approximately 3 weeks.

The model 700 was further formed to provide a simulated renal parenchyma. In particular, the calyx system (described below) is secured in a second container disposed within the first container, such as a plastic bag (e.g., 104) filled with a mixture of VYSE® Professional Grade ballistics gelatin (e.g. 112, which may be provided using, by non-limiting example, CustomCollagen, Illinois) and corn starch. The plastic bag represents the renal capsule surrounding the ballistics gel cortex. The addition of corn starch is critical to mimic the echogenicity of the renal cortex. After the kidney is solidified, it is secured to the simulator box (first container) wall and encapsulated by soft tissues. The comprehensive structures within the parenchyma and calyx components allow these models to be relevant for both PCNL procedural training and renal ultrasound imaging training.

Like the models 100 and 200, the model 700 further includes a third container disposed within the second container simulating a renal calyx system (e.g., kidney 102, and renal calyx 106). The renal calyx system be formed by embedding calcium carbonate stones inside a surgical glove, and the glove may be sealed to form the shape of a renal calyx. Latex tubing may then be secured into the glove to fill the calyx with yellow fluid via an external syringe. The fluid surrounding the kidney stones creates crescent-shaped targets on an associated ultrasound image captured by an ultrasound machine 702. In addition, the calyx system is customizable to create simulators with varied difficulty through the addition of hydronephrosis and stones of different sizes, shapes, and locations within the kidney. For the purposes of the study described herein, a 3 cm staghorn stone and a 1 cm lower pole stone were utilized to allow users to practice both upper and lower pole access.

Like, the models 100 and 200, the model 700 was further formed to provide simulated soft tissues. In particular, soft tissues may be formed using a combination of ballistics gel and silicone to mimic patient soft tissues and skin (e.g., 124 and 126). As described above, a mixture of corn starch and ballistics gel was used to add echogenicity to the soft tissues.

A layer of ballistics gel was placed at the base of the trainer to reduce needle collisions with the box and better mimic user haptic feedback. The kidney was placed on this base layer, and then a top ballistics gel layer was poured over the kidney. The thickness of the soft tissues can be varied to simulate obesity and create a more challenging model. Lastly, silicone was mixed with flesh pigment to create a skin-like surface above the soft tissues.

Like the models 100 and 200, the model 700 was further formed to provide one or more anatomical landmarks such as the ribs 128. In particular, for example, simulated ribs may be designed using any number or type of predetermined computer-aided design (CAD) models. Ribs 128 representing ribs 11 and 12 may be isolated and 3D printed by a fused deposition modeling 3D printer using polylactic acid (PLA) filament. After printing, the ribs 128 may be secured to a simulator box wall (e.g., secured to container 120 at an inferior angle above the kidney 102). The top layer (122A) of ballistics gel may be poured around the ribs 128 to accommodate rib palpation and identification from the superficial surface of the model. In addition, between the top layer of ballistics gel and the skin, two strips of silicone may be placed along the edge of the trainer box (120) to represent the paraspinous muscles.

Study: Testing and Simulation

Summary:

The materials and cost to create the model 700 were recorded over 5 iterative versions. Using a 5-point Likert scale survey, model fidelity was assessed by a group of international attending urologists with experience in US-PCNL and urology residents at the University of Arizona. Procedural confidence was assessed among medical students and residents before and after simulation training with the model. Confidence data was analyzed using a paired, two-tailed Student's t-test.

The model 700 costs ~$35 USD and takes ~1.5 hours to create. Compared to existing models it provides a comprehensive simulation experience. Mean overall model fidelity was 4.2±0.8, with high fidelity appreciated in the following features: resistance of skin and soft tissues (4.0±0.8); kidney stones/target calyx (4.1±0.9); visualization of needle (4.4±1.1) and fluid (4.4±0.9); echogenicity of cortex (4.2±0.7), stones (4.2±0.8), target calyces (4.1±0.8), and soft tissues (4.1±0.9). After training with the model 700, urology residents and medical students' procedural confidence increased significantly across all operational tasks. Accordingly, the model 700, as a low-cost simulator, provides a high-fidelity, affordable solution for teaching urologists how to perform US-PCNL.

Details of Study

Simulation Curriculum: Urology residents and medical students were provided with a full simulation training at the Arizona Simulation Technology and Education Center (ASTEC) located at the University of Arizona. This training included: a demographics survey, a procedural orientation, a simulator orientation, practice with the PCNL simulator (model 700), a pre-training procedural confidence survey, a recorded attempt at gaining appropriate access which was used for assessment of their performance, followed by a post-training confidence survey, and a 5-point Likert scale model fidelity survey.

In order to establish a proficiency benchmark, a group of international Urology attendings with expertise in Endourology were asked to. They were provided with a short training that included: orientation to the model 700 and its technical features. They were then asked to demonstrate appropriate percutaneous access. At the end of each session, the attendings were asked to complete the same 5-point Likert scale model fidelity survey. An overview of all participant experiences with the model can be found in Table 1 below. Successful access was gauged by the confirmation of fluid drip within 5 minutes for all participants.

At the ASTEC site, a simulator (implementation of the model 700) was set up with a Hitachi Aloka ProSound Alpha 7 ultrasound machine with a convex 5.7-1.8 MHz abdominal transducer (ultrasound probe). At the AUA site, the simulator was set up with a Hitachi Aloka Arietta 70 ultrasound with its convex 5-1 MHz abdominal transducer. An 18-gauge percutaneous access needle (704) with an echogenic tip was utilized for gaining percutaneous access into the collecting system.

Statistical Analysis: Survey data was compiled within a Microsoft Excel spreadsheet and all statistical analysis was performed in STATA. Paired student's t-tests were used to compare resident procedural confidence before and after the training with a p-value <0.05 considered statistically significant. Welch's t-test was used to determine differences between resident and attending model fidelity with a significance level of 5%.

Results: Demographic data for the medical students, residents, and attendings can be found in Table 2. A mean of 140 US-PCNL models were reported for the Urology attendings, compared to the novice Urology residents, where only a few reported previously assisting on an US-PCNL.

Procedural Confidence: All Urology residents and medical students participated in the simulation training and completed the pre- and post-training confidence surveys. Procedural confidence amongst residents and medical students significantly improved in all procedural tasks and overall confidence after training with the PCNL simulator (Table 3).

Model Fidelity: Model fidelity data from Urology residents and attendings was compiled and analyzed. Urology residents and attendings found training with the simulator to be realistic to performing a PCNL on a patient (Table 4). Despite the experience gap in US-PCNL between Urology residents and attendings, there were no significant differences in model fidelity between resident and attending surveys. Achieving successful renal access differed amongst medical students (%=0.75), Urology residents (%=0.89) and attendings (8/8=1.0).

Model Comparison: The model 700 was compared, during the study, with various conventional/competing models and it was found that the models of the present novel disclosure provide a unique and comprehensive set of features at an affordable cost of manufacture.

Discussion:

As the clinical utilization of US-PCNL continues to grow, the need for an affordable, high-fidelity training solution becomes more pertinent. The improved procedural confidence and high-fidelity ratings indicate that the US-PCNL model 700 provides a potential effective solution to bridge this educational gap. As a do-it-yourself model, the US-PCNL simulator provided by the model 700 has the advantage of customization that only takes approximately 90 minutes to build. The model 700 has the additional benefit of being customized to meet specific trainee needs. Kidney stone placement, renal capsule shape, and the amount of soft tissue can all be easily modified by the model maker; while the amount of hydronephrosis can be adjusted by the instructor. The flexibility and affordability of this high-fidelity model may be particularly useful for teaching PCNLs to health care providers in low-resource areas. Future directions allow for anatomic variations such as calyceal diverticulum, infundibular stenosis, duplicated collecting system, and a horseshoe kidney.

Medical student model fidelity survey data was not included due to their limited ultrasound and PCNL experience. The fidelity survey results among Urology residents and attendings provided encouraging feedback for the model, with an overall model rating of 4.2±0.8 (Mean±SD). It was confirmed that both the resident and attending participants rated the model similarly with the Welch's t-test, therefore the model fidelity data was combined. Meanwhile the fidelity survey results also helped to identify areas for improvement. Palpation and identification of paraspinous muscle landmark, feel of needle puncture through the renal capsule, and differentiation of renal capsule/cortex on ultrasound image were highlighted as needing improvement amongst the procedural steps. Based on these model fidelity results, the echogenicity of the renal cortex was optimized by cooling the top layer of ballistics gel prior to pouring it over the kidney. Continued adjustments to the thickness of the paraspinous muscles and thickness of the renal capsule may be beneficial to improve model fidelity. Future modifications will also aim to mimic practicing a supine PCNL approach.

Meanwhile the pilot data generated from this study demonstrated that there were differences in the ability of relative novices (medical students and urology residents) and experts (urology attendings) in achieving successful access. Historically this was considered construct validity, however this is a term now considered outdated and incorrect. However, by confirming this expected difference, the model 700 demonstrates that it could potentially serve as an assessment platform to evaluate a trainee's performance during a PCNL; i.e., by providing an actual context for this simulation. This is another possible aspect contemplated for this model, with the ultimate goal of eventually establishing the ability of the described simulator to offer a correlation with competency.

The results of the model comparison provide valuable insight regarding the challenges within US-PCNL simulation. While cadavers provide the gold standard for PCNL training, their use is limited by availability, reusability, storage, and cost. Biologic models are a more affordable training solution but pose similar challenges of storage and reusability. Educators using biologic models must also adjust their procedural steps to the unique anatomy of their animal model. Outside of biologic options, Virtual Reality (VR) simulators are an innovative solution to the storage and reusability concerns.

Non-biologic inanimate simulators provide the most affordable training solution, allow learners to practice with surgical equipment, and are easily stored and reused. The trade-off of conventional forms of these simulators is that they often sacrifice anatomical and procedural fidelity to maintain low costs. The present US-PCNL model 700 provides a cost-effective solution that addresses the structural and procedural deficits of alternative non-biologic simulators.

Conclusion: This study has demonstrated the feasibility of creating a low-cost simulator that provides a high-fidelity, affordable solution for teaching urologists how to perform US-PCNL. This model 700 provides a structurally comprehensive simulation experience compared to the existing models currently available.

The tables 1-4 referenced herein are as follows:

TABLE 1

Overview of simulated PCNL training format and surveys

| Components | Description | Medical Students & Urology Residents | Urology Attendings |
|---|---|---|---|
| Demographics Survey | Educational background, PCNL experience, and ultrasound experience | X | X |
| Procedural Confidence Survey | Pre- and post-procedural confidence survey with a 5-point Likert scale (1-Not Comfortable; 5-Very Comfortable) | X | — |
| Procedural Orientation | Review of US-PCNL access procedural steps in the prone position, followed by a demonstration | X | — |
| Simulator Orientation | Review of available instruments, equipment, and US-PCNL model features | X | X |
| PCNL Training | (Non-Limiting) Steps of simulated US-PCNL access:<br>1. Palpate ribs and paraspinous muscles<br>2. Place ultrasound probe parallel to ribs<br>3. Confirm direction of the ultrasound image in relation to probe placement<br>4. Identify kidney and kidney features on ultrasound image<br>5. Rotate ultrasound probe perpendicular to ribs<br>6. Identify target calyx<br>7. Optimize ultrasound probe position to the needle entry site<br>8. Insert percutaneous access needle<br>9. Direct the access needle toward the target calyx using ultrasound guidance<br>10. Remove the stylet | 30 minutes practice, followed by a proficiency demonstration of one simulated US-PCNL access | One simulated US-PCNL access |
| Model Fidelity Survey | Post-training model fidelity survey on a 5-point Likert scale (1-Least Realistic; 5-Most Realistic, performing a PCNL on a patient) | X | X |

TABLE 2

Demographic data from all users of the US-PCNL simulator

| Variable | Medical Students | Residents | Attendings |
|---|---|---|---|
| User Demographics (N) | 8 | 9 | 8 |
| Postgraduate year, N (%) | | | |
| I | 6 (75) | 2 (22) | n/a |
| II | 1 (13) | 2 (22) | n/a |
| III | | 2 (22) | n/a |
| IV | 1 (13) | 1 (11) | n/a |
| V | | 2 (22) | n/a |
| US-PCNL Experience (Mean + SD) | | | |
| Primary | 0 ± 0 | 0.3 ± 0.7 | 140 ± 100.6 |
| Assisted | 0 ± 0 | 3.3 ± 6.5 | |
| Present | 0 ± 0 | 0.4 ± 0.9 | |
| Simulation | 0.1 ± 0.4 | 1.6 ± 3.3 | 35 ± 37.7 |
| Ultrasound Experience (Mean + SD) Based on self-rating: (0 = none, 1 = 1-5, 2 = 6-10, 3 = 11-20, 4 = 21-40, 5 = 40+) | | | |
| Ultrasound Procedures | 0.3 ± 0.5 | 1.8 ± 1.6 | 4.6 ± 1.1 |
| Renal Ultrasounds | 0.3 ± 0.5 | 0.9 ± 0.8 | 5 ± 0 |
| Total Ultrasounds | 0.4 ± 0.5 | 2.1 ± 1.5 | 5 ± 0 |

TABLE 3

Reported urology resident and medical student procedural confidence before and after simulator use on a 5-point Likert scale (1-Not Comfortable; 5-Very Comfortable).

| Procedural Task | Average Resident Improvement | Significance | Average Medical Student Improvement | Significance |
|---|---|---|---|---|
| Palpation and identification of rib cage landmarks | 0.8 | P < 0.05 | 2.6 | P < 0.01 |
| Palpation and identification of paraspinous muscle landmarks | 1.2 | P < 0.01 | 3.1 | P < 0.01 |
| Positioning of ultrasound probe | 1.4 | P < 0.01 | 2.0 | P < 0.01 |
| Identification of kidney on ultrasound image | 1.2 | P < 0.01 | 2.0 | P < 0.01 |
| Identification of renal capsule, cortex, calyces, stone, and target calyx on ultrasound image | 0.8 | P < 0.05 | 2.5 | P < 0.01 |
| Identification of needle on ultrasound image | 1.1 | P < 0.01 | 2.6 | P < 0.01 |
| Advancing needle to target calyx | 1.4 | P < 0.01 | 3 | P < 0.01 |

TABLE 3-continued

Reported urology resident and medical student procedural
confidence before and after simulator use on a
5-point Likert scale (1-Not Comfortable; 5-Very Comfortable).

| Procedural Task | Average Resident Improvement | Significance | Average Medical Student Improvement | Significance |
|---|---|---|---|---|
| Remove needle stylet | 0.9 | $P < 0.05$ | 3 | $P < 0.01$ |
| Confirm access with fluid drip | 0.7 | $P < 0.05$ | 3.75 | $P < 0.01$ |
| OVERALL PROCEDURAL CONFIDENCE | 1.1 | $P < 0.01$ | 2.6 | $P < 0.01$ |

TABLE 4

Urology resident and attending fidelity surveys scored on a
5-point Likert scale (1-Least Realistic; 5-Most Realistic).

| Survey Question | Rating (Mean + SD) |
|---|---|
| PROCEDURE | |
| Palpation and identification of rib cage landmarks | 3.8 ± 0.8 |
| Palpation and identification of paraspinous muscle landmarks | 3.8 ± 1.0 |
| Resistance of skin and soft tissue layers to the passing of a needle | 4.0 ± 0.8 |
| Feel of needle puncture through the renal capsule | 3.6 ± 0.8 |
| Confirmation of access via fluid drip | 4.4 ± 0.9 |
| ULTRASOUND-GUIDANCE | |
| Echogenicity of soft tissue planes | 4.1 ± 0.9 |
| Echogenicity of kidney stones | 4.2 ± 0.8 |
| Echogenicity of kidney calyx targets | 4.1 ± 0.8 |
| Echogenicity of renal capsule | 4.1 ± 0.9 |
| Echogenicity of renal cortex | 4.2 ± 0.7 |
| Differentiation of renal capsule and cortex | 3.9 ± 1.0 |
| Differentiation of kidney stone and calyx targets | 4.1 ± 0.9 |
| Needle visibility and echogenicity | 4.4 ± 1.1 |
| OVERALL MODEL RATING | 4.2 ± 0.8 |

It is believed that the present disclosure and many of its attendant advantages should be understood by the foregoing description, and it should be apparent that various changes may be made in the form, construction, and arrangement of the components without departing from the disclosed subject matter or without sacrificing all of its material advantages. The form described is merely explanatory, and it is the intention of the following claims to encompass and include such changes.

While the present disclosure has been described with reference to various embodiments, it should be understood that these embodiments are illustrative and that the scope of the disclosure is not limited to them. Many variations, modifications, additions, and improvements are possible. More generally, embodiments in accordance with the present disclosure have been described in the context of particular implementations. Functionality may be separated or combined in blocks differently in various embodiments of the disclosure or described with different terminology. These and other variations, modifications, additions, and improvements may fall within the scope of the disclosure as defined in the claims that follow.

What is claimed is:

1. An anatomical model for nephrolithotomy training, comprising:
   a first container;
   a second container positioned within the first container, the second container at least partially filled with a mixture including ballistics gel and simulating a renal capsule;
   a third container disposed within the second container, the third container including one or more calcium carbonate stones and simulating a renal calyx, the third container further at least partially filled with a fluid; and
   one or more layers disposed around the third container, the one or more layers including ballistics gel,
   wherein implementation of the ballistics gel improves echogenicity during ultrasound-guided training procedures.

2. The anatomical model of claim 1, wherein the second container and the third container collectively simulate a kidney anatomy.

3. The anatomical model of claim 2, wherein the one or more layers are cooled prior to disposing the one or more layers around the third container optimizing the echogenicity of the kidney anatomy.

4. The anatomical model of claim 1, wherein the fluid is introduced to within the second container using a tubing and first and second openings defined along the second container and the third container respectively, the fluid being yellow to simulate urine.

5. The anatomical model of claim 4, wherein the one or more calcium carbonate stones mimic kidney stones and the fluid surrounds the kidney stones to create crescent-shaped targets viewable along an ultrasound image.

6. The anatomical model of claim 1, wherein the second container includes corn starch mixed with ballistics gel to mimic echogenicity of a natural renal cortex.

7. The anatomical model of claim 1, wherein the one or more layers further includes silicone.

8. The anatomical model of claim 1, further comprising a base layer of ballistics gel disposed along a bottom portion of the first container underneath the second container that suspends the second container over the bottom portion of the first container and reduces needle collisions with the first container and better mimic user haptic feedback during training.

9. The anatomical model of claim 8, wherein the second container is placed over the base layer of ballistics gel, the anatomical model further comprising a top layer including ballistics gel poured over the second container.

10. The anatomical model of claim 9, further comprising a 3D printed component printed using polylactic acid (PLA), the 3D printed component secured to a wall of the first container at an inferior angle above the second container, the 3D printed component simulating a rib.

11. The anatomical model of claim 10, wherein the top layer is poured around the 3D printed component to accommodate palpitation of the rib and identification from a superficial surface along the first container.

12. The anatomical model of claim 1, further comprising a strip of silicone placed between the one or more layers and the second container, the strip of silicone representing a paraspinous muscle.

13. The anatomical model of claim 1, further comprising a needle with an echogenic tip to accommodate access to within the second container by a trainee.

14. An anatomical model, comprising:
a plurality of simulated anatomical components, including:
  a kidney for ultra-sounded guided procedure training, the kidney including:
    a renal capsule,
    a renal calyx disposed within the renal capsule, and
    a kidney stone disposed within the renal calyx;
  a collecting system including yellow fluid to mimic urine; and
  a tissue layer simulated by a predetermined amount of ballistics gel formed along the kidney.

15. The anatomical model of claim 14, further comprising a container, wherein the kidney is disposed in the container and at least some of the predetermined amount of ballistics gel is disposed between a bottom side of the container and the kidney such that the kidney is at least partially suspended above the bottom side of the container.

16. The anatomical model of claim 14, further comprising a tube including a first end disposed within the renal capsule of the kidney, and second end opposite the first end extending outside the kidney, the tube mimicking a natural ureter.

17. The anatomical model of claim 14, wherein the kidney is formed using imaging data associated with a specific patient, such that the renal capsule and the renal calyx each resemble respective corresponding natural anatomy of the specific patient and the kidney stone resembles a natural kidney stone formed within the specific patient as identified using the imaging data.

18. The anatomical model of claim 14, wherein the collecting system provides feedback during training that a needle has reached a predetermined target by the yellow fluid emanating from a sheath of the needle.

19. A method, comprising:
forming a model, by:
  providing a first container;
  disposing a second container within the first container, the second container at least partially filled with a mixture including ballistics gel and simulating a renal capsule; and
  disposing a third container within the second container, the third container including a fluid and a calcium carbonate stone immersed within the fluid,
  wherein implementation of the ballistics gel improves echogenicity during an ultrasound-guided training procedure.

20. The method of claim 19, further conducting the ultrasound-guided training procedure using the model, by:
  placing an ultrasound probe along the model;
  confirming direction of an ultrasound image captured by the ultrasound probe in relation to placement of the ultrasound probe;
  identifying simulated kidney features of the model on the ultrasound image by the ultrasound probe;
  optimizing position of the ultrasound probe to an entry site for a needle; and
  accessing a predetermined target within the model by the needle.

* * * * *